United States Patent [19]

Horn

[11] 4,216,200

[45] Aug. 5, 1980

[54] DENTAL FILM AND METHOD OF FORMING THE SAME

[76] Inventor: William E. Horn, 1726 Professional Dr., Sacramento, Calif. 95824

[21] Appl. No.: 661,430

[22] Filed: Feb. 26, 1976

Related U.S. Application Data

[63] Continuation of Ser. No. 539,622, Jan. 9, 1975, abandoned.

[51] Int. Cl.² .......................... A61K 7/18; A61K 7/26
[52] U.S. Cl. ......................................... 424/52; 424/58
[58] Field of Search .................................... 424/52, 58

[56] References Cited

PUBLICATIONS

Jacobs, Am. Perfumer & Essential Oil Review, vol. 61, pp. 469, 471, Jun. 1953 "Flavoring Mouth Washes".
A. D. A. "Accepted Dental Therapeutics," 35th Ed., Jan. 1973, pp. 237-252, 256-258, 271-272.

*Primary Examiner*—Shep K. Rose
*Attorney, Agent, or Firm*—Tilton, Fallon, Lungmus & Chestnut

[57] ABSTRACT

A protective dental film formed by exposing surfaces of the oral cavity to a preparation capable of coacting with saliva to produce one or more tenacious and continuous barrier layers upon tooth and tissue surfaces.

6 Claims, No Drawings

DENTAL FILM AND METHOD OF FORMING THE SAME

RELATED APPLICATIONS

Reference is hereby made to prior copending application Ser. No. 539,622, filed Jan. 9, 1975, of which this application is a continuation, such prior application in turn making reference to prior copending (and now abandoned) application Ser. No. 324,874, filed Jan. 18, 1973, the benefit of the earlier filing date of which is claimed pursuant to 35 U.S.C. 120.

BACKGROUND

Considerable effort has been expended in the past to develop mouthwashes and treatment agents which have some chemical activity useful in retarding plaque, caries, and calculus formation. Conventional mouthwashes, purportedly designed to kill or control microbes which contribute to plaque and caries development, are not only generally ineffective as oral bactericides or bacteriostats but may even promote infection by oral bacteria and fungus by removing cornified epithelial layers and thereby allowing the escape of fluids and defensive cells which normally combat infection.

SUMMARY

One aspect of the present invention lies in the discovery of an oral rinse formula containing proportions of ingredients resulting in the formation of a tenacious protective film when said rinse is mixed with saliva in the mouth. Such discovery is particularly surprising in view of the fact that each of the ingredients has been previously known for use in mouthwashes, and that other rinses composed of different proportions of the very same ingredients, prepared and tested as disclosed herein, appear incapable of producing similar results. The protective film produced by repeated (daily) use of such oral rinse formula has been found to give teeth a high luster or sheen, reduce plaque attachment, diminish calculus attachment, reduce interproximal and gingival caries, decrease swelling of gingival tissue, reduce stains and their formation, reduce the discomfort of Apthos ulcers and promote the healing of such ulcers, as well as of cuts and abrasions in the mouth, and reduce and control sensitivity of areas about the crowns and roots of teeth.

In the best mode presently known for carrying out the invention, the rinse formula contains, for each 1,000 to 4,000 milliliters (ml) of oral rinse, 22 to 220 milligrams (mg) of sodium fluoride, 1.0 grams (gm) menthol, 1.3 ml Oil of Cinnamon, 0.5 ml Oil of Cloves, 0.8 gm sodium saccharine, 60.0 ml ethyl alcohol, 15 gm purified talc, 24 to 50 drops of food coloring, and the remainder (to make 1,000 to 4,000 ml), distilled water. The preparation is used by first brushing the teeth in a normal manner, then rinsing the mouth with a small amount of the preparation, and then simply spitting out the excess and avoiding the introduction of any other liquids or food into the mouth for a period of several minutes. While brushing of the teeth, followed by normal rinsing with water, is desirable as a first step in the treatment procedure, its primary purpose is to remove loose material which would hinder the adherence of one layer of film to the layer below.

DETAILED DESCRIPTION

While the precise mechanism of the protective barrier is not fully known, three of the ingredients of the rinse, in specific proportions and in the presence of the fluoride ion, are understood to combine or coact with saliva in producing an essentially continuous film upon the teeth and upon other surfaces in the mouth. The three ingredients, menthol, Oil of Cloves and Oil of Cinnamon, must not only be present, but must be present in the relative proportions (by weight) of approximately 10:5:13, respectively. By contrast, considerable latitude in the fluoride concentration is allowable. For example, in a solution having a total volume of 1,000 to 4,000 milliliters, the amount of sodium fluoride may fall within the range of 10 to 300 milligrams, the preferred range being believed to be about 22 to 220 milligrams. The mechanism of the action of sodium fluoride is unclear but it appears that there is no complexing of the fluoride ion either in the preparation of the dental solution or in the combining of that solution with saliva. Instead, the fluoride ion concentration remains relatively constant, indicating that it may possibly function as a catalyst in the formation of the protective film.

It has been speculated that proteins in saliva may become cross-linked, coagulated, precipitated, or coacervated in admixture with the one or more of the three main ingredients of the rinse in producing the stable, transparent, and tenacious film; however, while amylase, commonly regarded as being the most active ingredient in saliva, is such a protein, there is insufficient present information concerning its chemical formula to ascertain whether any of its more active groups interconnect as part of the film-forming mechanism.

The presence of fluoride, without the coaction of the three critical ingredients of the solution, does not produce the desired coating in combination with saliva. Attention is directed to Examples 2 and 3 which disclose formulations similar to that of Example 1 but which, for reasons not fully known, have failed to result in a solution capable of coacting with saliva to produce an effective barrier film.

Whatever the theoretical explanation, it is to be emphasized that the film requires the presence of saliva for its formation, unlike the action of conventional rinses or mouthwashes which tend to destroy or inactivate saliva proteins. Biuret tests reveal that saliva proteins remain detectable following exposure of saliva to the active ingredients of the dental solution formula, while the color of the reaction might be interpreted as indicating some modification or interaction of such protein in consequence of such exposure (see Example 6).

Brushing of the teeth prior to use of the dental rinse is believed desirable to remove loosely adhered food materials and bacterial plaque. Unless the rinse is used on a regular basis, the chewing and swallowing activity of the oral cavity which includes, the washing action of saliva and the mechanical action of the tongue and other oral muscles will eventually remove the film. The interval of application of the rinse may vary from two or more times daily to only a single daily application, preferably before retiring, although it is believed that some diminished beneficial effects would also be achieved with applications of even lesser frequency.

Intimate mixing of the solution with saliva is important, followed by a definite period of oral inactivity (refraining from introducing other liquids and food into the mouth) immediately after the mixing steps. Particularly effective results have been achieved in a procedure involving a mixing step of approximately one minute, after which the patient spits out the excess solution and then refrains from eating, drinking, or rinsing the mouth with any other fluid for a period within the range of approximately 10 to 20 minutes. Somewhat shorter periods might be possible, with a commensurate decrease in effectiveness, and even longer periods may be preferable.

One of the first noticeable effects of such treatment has been increased sheen, brightness, and smoothness of the teeth, apparent to both patients and (usually) observers, as early as the second day of such treatment. Adherence of plaque colonies is clearly reduced, presumably because of the extreme smoothness of the tenacious film. Those colonies which do appear are easily dislodged by water irrigating devices or by brushing. Over a period of 6 to 12 weeks of treatment, plaque reduction has been found to exceed 60 percent. With such a decrease in plaque, a reduction in caries would be expected and has indeed been observed.

A decrease in plaque would also be expected to be accompanied by a reduction in calculus and such reduction has also been noticed. Subgingival and supragingival calculus of up to eight years duration has been spontaneously ejected from tooth and root surfaces during an initial two to three weeks of use of the rinse, and prior to any dental scaling. Calculus formation following prophylaxis has been found to be less than 20 percent of the original volume for patients having yearly dental examinations, and less than 10 percent for patients having semi-annual examinations.

The film also appears to act as a protective covering which somehow seals off exposed nerve endings. A substantial reduction in root sensitivity has been observed. Patients previously requiring local anesthetics for simple scaling procedures and those who have had gingivectomies have reported to be free of pain during scaling, without use of such anesthetics, following use of the oral rinse for a period of two to three weeks.

The pain of Apthos ulcers has been found to be markedly reduced by frequent use of the oral rinse. By repeated use of the solution when pain has occurred, such ulcers have become pain free in hours and have generally healed by the third day. Similar results have been observed in connection with cuts, bites, scrapes, or burns in the mouth. The size of the lesion and the number of such lesions has been observed to be directly related to the speed of pain relief and healing. In the case of chronic Apthos ulcers, the continued use of the oral rinse appears to prevent the initial eruption of the lesion in the vast majority of cases studied.

Stains on natural teeth and dental appliances are markedly reduced, and those that form are readily removed, following use of the oral rinse. In general, dental appliances have been found to remain clean and free of stain and calculus when the oral rinse is regularly used.

The invention may be more clearly understood from consideration of the following illustrative examples:

EXAMPLE 1

A dental rinse embodying the present invention was prepared according to the following formula:

| | |
|---|---|
| NaF (Reagent Grade) (Baker & Adams, Morristown, N.J.) | 220 mg |
| Menthol (Gentry International, Inc., Fairlawn, N.J.) | 1.0 gm |
| Oil of Cinnamon (Robinson Laboratories, Inc., San Francisco, Calif.) | 1.3 gm |
| Oil of Cloves (Gentry International, Inc., Fairlawn, N.J.) | 0.5 gm |
| Sodium Saccharine (Merck & Co., Rahway, N.J.) | 0.8 gm |
| Ethyl Alcohol (Commercial Solvents Corp., New York, N.Y.) | 60.0 ml |
| Purified Talcum (magnesium silicate) (Merck & Co., Rahway, N.J.) | 15.0 gm |
| Red Food Coloring (Schillings) (McCormick & Company, Inc., Baltimore, Md.) | 24 drops |

In preparing the rinse, the two oils were first added to the purified talcum and distilled water was then added to bring the volume to 700 ml. The menthol was dissolved in the ethyl alcohol which was then added to the talcum, oil and water, and the total volume was increased by the addition of distilled water to 1,000 ml. Following filtration, the red food coloring and saccharine were added, the total volume was adjusted by the addition of distilled water to 4,000 ml, and the sodium fluoride was added. The preparation was then allowed to stand for five or seven days and was again filtered. While talcum was used as a clarifying or purifying material, and to assist in dissolving the other ingredients, its presence is not critical and, if used, its amount may be varied.

EXAMPLE 2

Following the same procedure set forth in Example 1, a solution was prepared using the same ingredients from the same sources in the following proportions:

| | |
|---|---|
| NaF | 44 mg |
| Menthol | 0.25 gm |
| Oil of Cinnamon | 0.65 gm |
| Oil of Cloves | 0.25 gm |
| Sodium Saccharine | 0.2 gm |
| Ethyl Alcohol | 15.0 ml |
| Purified Talcum (magnesium silicate) | 3.75 gm |
| Red Food Coloring | 20 drops |

EXAMPLE 3

Following the same procedure set forth in Example 1, a solution was prepared using the same ingredients from the same sources in the following proportions:

| | |
|---|---|
| NaF | 5,000 mg |
| Menthol | 0.5 gm |
| Oil of Cinnamon | 1.3 gm |
| Oil of Cloves | 0.5 gm |
| Sodium Saccharine | 0.4 gm |
| Ethyl Alcohol | 30.0 ml |
| Purified Talcum (magnesium silicate) | 15.0 gm |
| Red Food Coloring | 12 drops |

EXAMPLE 4

The preparations formulated and compounded as set forth in Examples 1 through 3 were tested by over 20 subjects in accordance with the following instructions: (1) brush teeth; (2) rinse mouth with water; (3) take one-half teaspoon of liquid preparation; (4) thoroughly rinse mouth with such solution, forcing solution between and around teeth and gums, and mixing solution with saliva; (5) spit out excess; (6) refrain from drinking, rinsing, or eating for at least 10 minutes following such treatment; (7) use at least once or more times daily.

The preparations of Examples 2 and 3, when repeatedly used as above, produced no noticeable effects except for a possible reduction in caries activity. In contrast, repeated use of the preparation of Example 1 brought about the following results not produced by the preparations of Examples 2 and 3: (1) teeth had increased luster and sheen; (2) teeth were smoother feeling to the tongue and even rough areas of the teeth felt substantially smoother than before; (3) dental plaque was either entirely absent from the teeth or was greatly reduced; (4) calculus was diminished in mouths which had not been scaled and polished prior to use of such preparation; (5) gingival tissue swelling was noticeably diminished.

EXAMPLE 5

A comparison study (double blind with a crossover) was conducted using a rinse prepared in accordance with Exhibit 1 (identified below as preparation A), and a second rinse identical thereto except for the omission of sodium fluoride (identified below as preparation B). Each subject was instructed to brush his teeth twice daily, followed by an oral rinse with 15 ml of one of the unidentified preparations. Excess rinse was to be expectorated and no further fluids or foods were to be introduced into the mouth for 15 minutes thereafter. After seven days, each subject was instructed to follow the same procedure for an additional seven days using the other unidentified preparation. At the end of the 14 days test period, the 23 subjects who completed all parts of the test were examined and the extent of plaque formation was analyzed and recorded with the following results:

| Preparation A (Mean Plaque Score) | Preparation B (Mean Plaque Score) | Percent of Plaque Reduction Using Preparation A |
|---|---|---|
| 11.20 | 18.27 | 38.75% |

A similar comparison study was conducted, the only differences being that dosage was reduced from 15 ml to 2.5 ml and the test period was extended to seven weeks. At the end of three weeks, the test results were as follows:

| Preparation A (Mean Plaque Score) | Preparation B (Mean Plaque Score) | Percent of Plaque Reduction Using Preparation A |
|---|---|---|
| 9.25 | 18.27 | 40.37% |

The results at the end of the full seven week period were as follows:

| Preparation A (Mean Plaque Score) | Preparation B (Mean Plaque Score) | Percent of Plaque Reduction Using Preparation A |
|---|---|---|
| 7.16 | 18.27 | 60.81% |

EXAMPLE 6

The action of the dental rinse of Example 1 in admixture with saliva, and a comparison of that action with other standard mouthwashes, is illustrated by the following analysis using the biuret method for protein analysis (Reinhold, J. G., Standard Methods of Clinical Chemistry, Vol. 1, p. 88, 1953).

To eight test tubes containing samples of human saliva (pH of about 6.5) was added measured amounts of seven commercial mouthwashes and an oral rinse solution prepared in accordance with Example 1. The results were as follows:

| Preparation | Protein Test Results |
|---|---|
| Lavoris (pH 4.5) | Negative |
| Listerine (pH 5) | Negative |
| Cepacol (pH 6.5) | Negative |
| Micrin (pH 6.2) | Negative |
| Colgate (pH 5.8) | Negative |
| Scope (pH 6) | Negative |
| Chloroseptic (pH 9) | Negative |
| Example 1 Rinse (pH 5.5) | Positive |

All of the standard commercial mouthwashes were found to destroy saliva proteins (enzymes). With the oral rinse prepared in accordance with Example 1, saliva proteins were not destroyed, as indicated by the positive results. However, instead of a blue flocculent precipitate, the precipitate was of a reddish-blue color. In addition, the pH of the mixture increased from 6.5 (of saliva) and 5.5 (for the dental rinse in admixture therewith) to above 7. Although it is known that some proteins in the presence of an acid react to give a basic pH, the precise reasons for the change in this instance are not fully known.

EXAMPLE 7

Photomicrograms taken by a scanning electron microscope of natural tooth (enamel) surfaces and artificial tooth (porcelain) surfaces, treated with a solution prepared in accordance with Example 1, and with modified solutions in which selected constituents of the Example 1 solution were omitted, reveal that menthol, Oil of Cloves, Oil of Cinnamon, and sodium fluoride must all be present with saliva for the formation of a continuous coating, and that other constituents (ethyl alcohol, red food coloring and saccharine) may be omitted without any apparent difference in such coating.

The test series was conducted in vitro on enamel and porcelain surfaces which were first washed thoroughly and dried. The test material was then painted on the surface of the sample and dried, and the dry treated surface then washed with a pulsing stream of water at relatively low pressure (discharged from a Water Pik instrument) and finally dried. The painting, drying, washing and final drying steps were repeated a total of six times.

Those surfaces treated only with the solution of Example 1 (without saliva) had no observable film formed thereon; such surfaces appeared essentially the same as untreated surfaces used as controls. The porcelain surfaces treated with saliva alone failed to reveal any film. The enamel surfaces similarly treated only with saliva did indicate a coating but such coating lacked the continuity of a film; it was instead characterized by wide fissures or cracks.

By contrast, the surfaces treated with a mixture of equal volume of solution of Example 1 and saliva revealed a relatively smooth continuous coating or film. Multiple repetitions of such tests with saliva and modifications of the solution of Example 1 in which selected constituents and combinations of constituents were omitted indicated that the continuous film would not form if Oil of Cloves, Oil of Cinnamon, menthol, and sodium fluoride, or any one or more of those ingredients, were omitted. Other tests in which sacchraine, red food coloring, and ethyl alcohol (or combinations thereof) were omitted yielded photomicrograms in which the appearance of the surface and the film appearing thereon were similar to those in which all of the ingredients were present, thereby indicating that such saccharine, red food coloring and ethyl alcohol are not required to be present in the solution of Example 1 to form a film when mixed with saliva and applied to an enamel or porcelain surface.

EXAMPLE 8

An illustration of the effect of a solution prepared in accordance with Example 1 on surface tension when a mixture of such solution and saliva is in contact with a clean tooth surface is represented in the following goniometric data:

| Liquid | Substrate | Contact Angle | Time Min. |
|---|---|---|---|
| $H_2O$ (distilled) | Clean Tooth | 62° | 0–6 |
| Saliva | Clean Tooth | 62° | 0–6 |
| Example 1 Solution | Clean Tooth | 61° | 0–6 |
| Example 1 Solution plus Saliva | Clean Tooth | 44° | Initial |
| | | 40° | in 2 min. |
| | | 32° | in 4 min. |
| | | 20° | in 6 min.* |

*Unable to measure angle after 6 minutes.

Reference is also made to the findings of Example 7 in which saliva was shown to have little if any tendency to wet procelain but, upon being mixed with a solution prepared in accordance with Example 1, the combination formed a continuous coating on the porcelain surfaces. Such results indicate that the dental solution lowers surface tension and improves the wetting effect of both constituents (saliva and the dental solution) when mixed with saliva.

While in the foregoing I have disclosed an embodiment of the invention in considerable detail for purposes of illustration, it will be understood by those skilled in the art that many of those details may be varied without departing from the spirit and scope of the invention.

I claim:

1. A dental solution suitable for use in forming a protective barrier on oral surfaces when mixed with saliva, consisting essentially of sodium fluoride in an aqueous solution containing menthol, Oil of Cloves, and Oil of Cinnamon in the proportions by weight of approximately 10:5:13, respectively, said sodium fluoride being present in the range of about 0.1 to 3.0 milligrams per total solution volume of approximately 10 to 40 milliliters.

2. The solution of claim 1 in which said proportions of menthol, Oil of Cloves, and Oil of Cinnamon are in milligrams per total solution volume of about 10 to 40 milliliters.

3. The solution of claim 1 in which said sodium fluoride is present in the range of about 0.22 to 2.2 milligrams.

4. A method of forming a protective coating upon tooth and oral tissue surfaces, comprising the steps of introducing into the mouth an oral solution capable of coacting with saliva to produce a transparent and tenacious film upon said surfaces, mixing said solution with saliva in the mouth, and thereafter retaining in the mouth enough of said solution for a period sufficient to form said film upon said surfaces, said solution consisting essentially of sodium fluoride in an aqueous solution containing menthol, Oil of Cloves, and Oil of Cinnamon in the proportions by weight of approximately 10:5:13, respectively, said sodium fluoride being present in the range of about 0.1 to 3.0 milligrams per total solution volume of approximately 10 to 40 milliliters.

5. The method of claim 4 in which said proportions of menthol, Oil of Cloves, and Oil of Cinnamon are in milligrams per total solution volume of about 10 to 40 milliliters.

6. The method of claim 4 in which said sodium fluoride is present in the range of about 0.22 to 2.2 milligrams.

* * * * *